(12) United States Patent
Orihashi et al.

(10) Patent No.: US 11,512,274 B2
(45) Date of Patent: Nov. 29, 2022

(54) MICROORGANISM SAMPLING DEVICE

(71) Applicants: SATAKE CORPORATION, Tokyo (JP); MOL ENGINEERING CO., LTD., Tokyo (JP)

(72) Inventors: Keisuke Orihashi, Tokyo (JP); Yoshihisa Saita, Tokyo (JP); Shuji Miyai, Tokyo (JP)

(73) Assignee: SATAKE CORPORATION, Tokyo (JP)

( * ) Notice: Subject to any disclaimer, the term of this patent is extended or adjusted under 35 U.S.C. 154(b) by 656 days.

(21) Appl. No.: 16/486,946

(22) PCT Filed: Feb. 20, 2018

(86) PCT No.: PCT/JP2018/006009
§ 371 (c)(1),
(2) Date: Aug. 19, 2019

(87) PCT Pub. No.: WO2018/151316
PCT Pub. Date: Aug. 23, 2018

(65) Prior Publication Data
US 2020/0231920 A1    Jul. 23, 2020

(30) Foreign Application Priority Data

Feb. 20, 2017 (JP) .............................. JP2017-029399

(51) Int. Cl.
*C12M 1/00* (2006.01)
*G01N 1/04* (2006.01)
(Continued)

(52) U.S. Cl.
CPC ............. *C12M 29/04* (2013.01); *B01D 29/23* (2013.01); *B01D 29/908* (2013.01); *B01D 29/92* (2013.01);
(Continued)

(58) Field of Classification Search
CPC ...... C12M 29/04; C12M 23/38; C12M 27/10; B01D 29/23; B01D 29/908; B01D 29/92;
(Continued)

(56) References Cited

U.S. PATENT DOCUMENTS 2,743,019 A * 4/1956 Kovacs .................. B01D 29/58
210/493.1
3,353,680 A * 11/1967 Niebergall ........... B01D 27/106
210/DIG. 17

(Continued)

FOREIGN PATENT DOCUMENTS

CN        101046432 A    10/2007
CN        103925955 A    7/2014
(Continued)

OTHER PUBLICATIONS

Extended European Search Report dated Dec. 1, 2020 in European Patent Application No. 18753664.1.
(Continued)

*Primary Examiner* — Madeline Gonzalez
(74) *Attorney, Agent, or Firm* — Faegre Drinker Biddle & Reath LLP (57) ABSTRACT

A microorganism sampling device includes: a head part that has a water supply channel to which a water supply pipe for supplying sample water can be connected; a housing part to an upper part of which the head part can be detachably attached; a frame-structured tube; a tubular filter that is arranged within the tubular body; a cup that communicates with the tubular filter and is attached to one end of the tube body; and a cap that has a channel communicating with the tubular filter and is attached to the other end of the tube body. The microorganism sampling device further includes a filter part housed in the housing part, in which a bottom part of the cup is supported by a bottom part of the housing (Continued)

part. The head part is attached to an upper part of the housing part.

9 Claims, 8 Drawing Sheets

(51) Int. Cl.
  *C12M 3/04* (2006.01)
  *B01D 29/92* (2006.01)
  *B01D 29/94* (2006.01)
  *B01D 35/30* (2006.01)
  *B01D 29/90* (2006.01)
  *B01D 29/23* (2006.01)
  *B63J 4/00* (2006.01)

(52) U.S. Cl.
  CPC ............ *B01D 29/94* (2013.01); *B01D 35/30* (2013.01); *C12M 23/38* (2013.01); *C12M 27/10* (2013.01); *G01N 1/04* (2013.01); *B01D 2201/0415* (2013.01); *B01D 2201/303* (2013.01); *B63J 4/002* (2013.01)

(58) Field of Classification Search
  CPC .................. B01D 29/94; B01D 35/30; B01D 2201/0415; B01D 2201/303; B01D 24/42; B01D 24/44; B01D 29/11; B01D 29/90; G01N 1/04; G01N 1/10; G01N 2001/4088; G01N 1/40; B63J 4/002; Y02A 20/20; B63B 13/00
  USPC ......... 210/440–443, 92, 305, 298, 299, 455, 210/248, 314, 335, 437, 457; 435/308.1
  See application file for complete search history.

(56) References Cited

U.S. PATENT DOCUMENTS

| | | |
|---|---|---|
| 5,820,767 A | 10/1998 | Kane et al. |
| 2010/0297691 A1 | 11/2010 | Ribeiro et al. |
| 2012/0003626 A1 | 1/2012 | Kshirsagar et al. |
| 2015/0292995 A1 | 10/2015 | Kshirsagar et al. |
| 2016/0370261 A1 | 12/2016 | Fukuyo et al. |

FOREIGN PATENT DOCUMENTS

| | | |
|---|---|---|
| CN | 203785929 U | 8/2014 |
| CN | 205404182 U | 7/2016 |
| JP | H05-306978 A | 11/1993 |
| JP | 2000-517171 A | 12/2000 |
| JP | 2005-291940 A | 10/2005 |
| JP | 2008-286708 A | 11/2008 |
| JP | 2009-115500 A | 5/2009 |
| JP | 4845855 B2 | 12/2011 |
| JP | 2014-204726 A | 10/2014 |
| JP | 2015-14516 A | 1/2015 |
| KR | 2012-0100587 A | 9/2012 |

OTHER PUBLICATIONS

The Notification of the First Office Action dated Jul. 22, 2021 in Chinese Patent Application No. 2018800128872 (7 pages) with an English Translation (9 pages).

\* cited by examiner

MICROORGANISM SAMPLING DEVICE

CROSS REFERENCE TO PRIOR APPLICATIONS:

This application is the National Stage of International Application No. PCT/JP2018/006009 filed Feb. 20, 2018 and claims benefit of Japanese Application No. 2017-029399 filed on Feb. 20, 2017, which are herein incorporated by reference in their entirety.

TECHNICAL FIELD

The present invention relates to a microorganism sampling device that samples, in a living state, microorganisms such as planktons existing in water such as ballast water.

BACKGROUND ART

In the conventional arts, a device that samples microorganisms existing in ballast water has been proposed in order to investigate the population of living microorganisms contained in the ballast water (for example, see Patent Literature 1).

Figure 8:
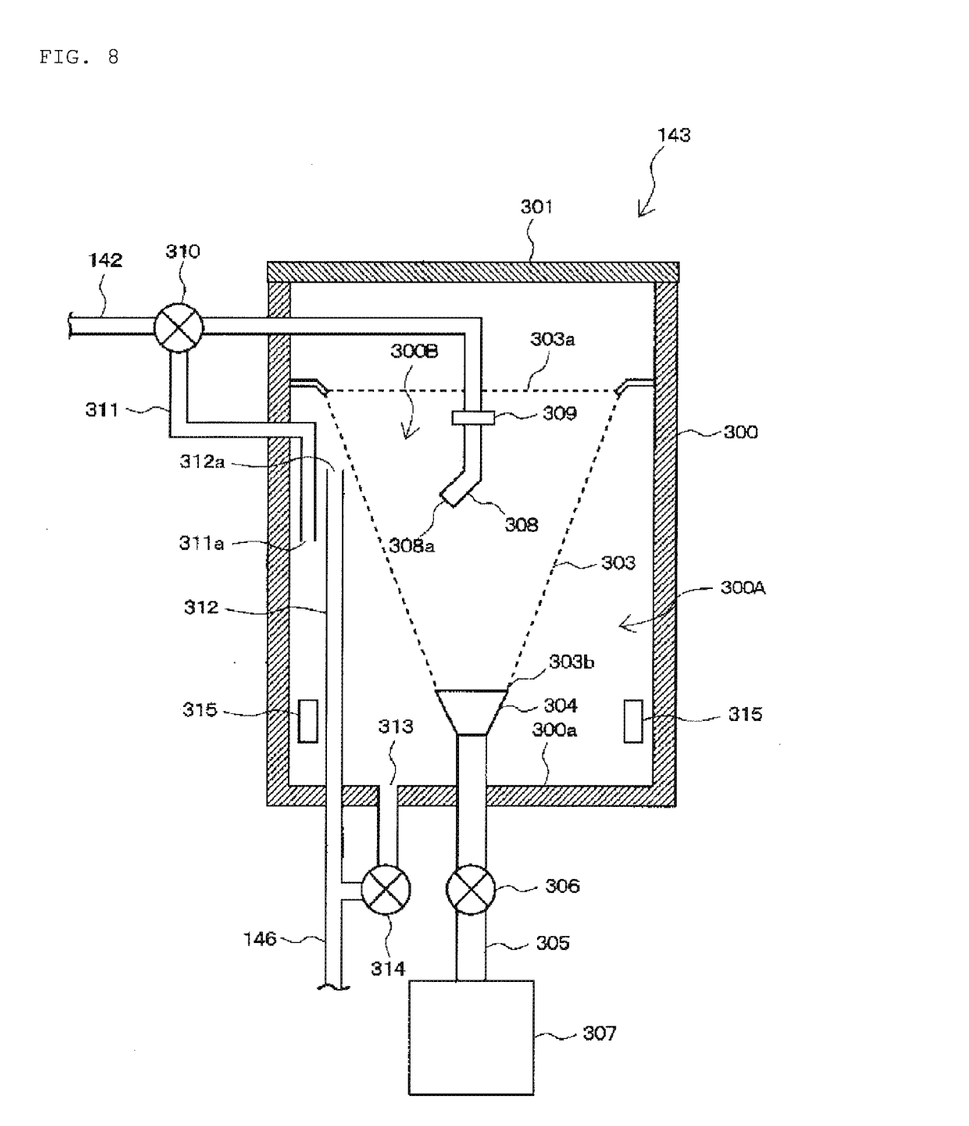
FIG. 8 shows a sampling device for aquatic organisms described in Patent Literature 1.

FIG. 8 shows a sampling device for aquatic organisms that is described in Patent Literature 1.

The sampling device described in Patent Literature 1 includes a configuration in which a filter cloth 303 in a substantially inverted cone shape is placed in a water storage container 300, thereby partitioning a space 300A outside the filter cloth 303 and a space 300B inside the filter cloth 303, an overflow pipe 312 and a drain port 313 are provided in the space 300A outside the filter cloth 303, and a storage part 304 is connected to a lower end opening 303b of the filter cloth 303.

The above sampling device continuously supplies sample water to the inside of the filter cloth 303 of the water storage container 300 and discharges the sample water from the overflow pipe 312, thereby sampling aquatic organisms while the water level in the water storage container 300 is kept constant.

According to the sampling device, water in the water storage container 300 is drained from the drain port 313 after a required amount of sample water is supplied and thereby, concentrated water in a state where aquatic organisms that are too large to pass through the filter cloth 303 are concentrated is stored in the storage part 304 and the concentrated water can be collected via a water sampling pipe 305 connected to a bottom part of the storage part 304.

The sampling device described in Patent Literature 1, which supplies sample water to the storage container 300 by a water sampling pipe 142, has a problem in that the size and complexity of the device are increased because the water sampling pipe 142 is integrally incorporated into the water storage container 300 so as to be arranged from an upper part of a side part of the water storage container 300 to an inner part thereof and toward an inside of an upper end opening 303a of the filter cloth 303.

In addition, in the above sampling device, the water sampling pipe 142 and the like are arranged inside the water storage container 300 and therefore, it is difficult to perform operations such as cleaning inside the water storage container 300 and replacement of the filter cloth 303, which causes a problem in maintainability.

CITATION LIST

Patent Literature

[Patent Literature 1] Japanese Patent No. 4845855

SUMMARY OF INVENTION

Technical Problem

Therefore, an object of the present invention is to provide a microorganism sampling device that has a simple and compact configuration and also has excellent maintainability.

Solution to Problem

In order to achieve the above object, a microorganism sampling device of one aspect of the present invention is provided which samples microorganisms existing in water and includes: a lid part that has a water supply channel to which a water supply pipe for supplying sample water can be connected; a housing part to which the lid part is detachably attached or which is detachably attached to the lid part; and a filter part that is housed in the housing part and filters the microorganisms from the sample water.

The microorganism sampling device of one aspect of the present invention includes: a head part that has a water supply channel to which a water supply pipe for supplying sample water can be connected;

a housing part to an upper part of which the head part is detachably attached; and a filter part that includes a frame-structured tube body, a tubular filter arranged within the tube body, a cup communicating with the tubular filter and attached to one end of the tube body, and a cap having a channel communicating with the tubular filter and being attached to another end of the tube body, in which the filter part is housed in the housing part and a bottom part of the cup is supported by a bottom part of the housing part.

The head part is attached to an upper part of the housing part so as to make a water supply channel of the head part and a channel of the cap of the filter part communicate with each other, thereby allowing sample water supplied from the water supply channel of the head part to be supplied into the tubular filter of the filter part.

In the microorganism sampling device of one aspect of the present invention, preferably, the head part further includes a water discharge channel to which a water discharge pipe for discharging sample water can be connected; and the head part is attached to the upper part of the housing part so as to make the water discharge channel of the head part and a space outside the filter part communicate with each other, thereby allowing the sample water having passed through the tubular filter of the filter part to be discharged from the water discharge channel of the head part.

In the microorganism sampling device of one aspect of the present invention, preferably, a discharge port for discharging concentrated water in which microorganisms that are too large to pass through the tubular filter are concentrated is provided on the bottom part of the cup; and a concentrated water discharge part for discharging the concentrated water from the discharge port of the cup is provided on the bottom part of the housing part.

In the microorganism sampling device of one aspect of the present invention, preferably, a sample water drain part for draining sample water remaining in the housing part is provided on the bottom part of the housing.

In the microorganism sampling device of one aspect of the present invention, preferably, a rectifying part for swirling the sample water supplied into the tubular filter is provided within the channel of the cap.

In the microorganism sampling device of one aspect of the present invention, the lid part is a base part, the housing part is detachably attached to an upper part of the base part, the base part includes an opening for supplying to the inside of the filter part the sample water supplied to the base part, the filter part has a tubular filter and a cup that is attached so as to communicate with the tubular filter, the cup has an opening on a bottom part of the cup and the bottom part of the cup is supported by the base part, and the sample water is supplied from the opening provided on the base part to the inside of the filter part via the opening provided on the bottom part of the cup.

In the microorganism sampling device of one aspect of the present invention, the lid part is a base part, the housing part is detachably attached to an upper part of the base part, the base part includes a pipe for spouting to the inside of the filter part the sample water supplied to the base part, the filter part has a tubular filter and a cup that is attached so as to communicate with the tubular filter, and the cup has a through hole for inserting the pipe on a bottom part of the cup and the bottom part of the cup is supported by the base part.

In the microorganism sampling device of one aspect of the present invention, preferably, the base part further has a water discharge channel to which a water discharge pipe for discharging sample water having passed through the filter part can be connected, and the base part is attached to a lower part of the housing part so as to make the water discharge channel of the head part and a space outside the filter part communicate with each other, thereby allowing the sample water having passed through the tubular filter of the filter part to be discharged from the water discharge channel of the base part.

In the microorganism sampling device of one aspect of the present invention, preferably, the pipe includes an outflow port for discharging, from the cup, concentrated water in which microorganisms that are too large to pass through the tubular filter are concentrated; and the base part includes a concentrated water discharge part for discharging the concentrated water flowing out from the outflow port of the pipe.

In the microorganism sampling device of one aspect of the present invention, preferably, the filter part includes a frame-structured tubular body provided on the inside of the tubular filter and supporting the tubular filter.

The microorganism sampling device of one aspect of the present invention is preferably a portable microorganism sampling device including a frame having a stand on its back surface and fixing a microorganism sampling device according to any one of the above descriptions to the frame.

The microorganism sampling device of one aspect of the present invention includes a head part having a water supply channel and allows a water supply pipe for supplying sample water to be connected to the water supply channel, and therefore, does not need to integrally incorporate the water supply pipe, thereby achieving a simple and compact configuration.

In addition, the microorganism sampling device of one aspect of the present invention allows the water supply channel of the head part and the channel of the cap of the filter part to communicate with each other by attaching the head part to the upper part of the housing part, thereby achieving a simple and compact configuration.

Further, the microorganism sampling device of one aspect of the present invention allows the filter part to be removed from the housing part by removing the head part from the upper part of the housing part and therefore, for example, operations such as cleaning of the housing part and replacement of the tubular filter (for example, as a disposable tubular filter) of the filter part can be easily performed, thereby achieving excellent maintainability, too.

In the microorganism sampling device of one aspect of the present invention, when the head part further having a water discharge channel is provided and a water discharge pipe for discharging sample water can be connected to the water discharge channel, it is not necessary to integrally incorporate the water discharge pipe and thus a further simple and compact configuration can be achieved.

In addition, in the microorganism sampling device of one aspect of the present invention, when the head part is attached to the upper part of the housing part and thereby, the water discharge channel of the head part and a space outside the filter part is made to communicate with each other, it is not necessary to provide an overflow pipe. In accordance with this, a further simple and compact configuration can be achieved.

In addition, in the microorganism sampling device of one aspect of the present invention, the head part, housing part, and filter part are assembled and thereby, sample water supplied from the water supply channel of the head part can be supplied into the tubular filter of the filter part and the sample water having passed through the tubular filter can be discharged from the water discharge channel of the head part; and thus, a simple and compact configuration can be achieved.

Further, the microorganism sampling device of one aspect of the present invention is configured such that sample water supplied from the water supply channel of the head part can be supplied into the tubular filter of the filter part and the sample water having passed through the tubular filter can be discharged from the water discharge channel of the head part; thus allowing a large amount of sample water to be continuously treated.

In the microorganism sampling device of one aspect of the present invention, when a discharge port for discharging concentrated water in which microorganisms that are too large to pass through the tubular filter are concentrated is provided on the bottom part of the cup and a concentrated water discharge part for discharging the concentrated water from the discharge port of the cup is provided on the bottom part of the housing part, the concentrated water stored in the cup can be collected by a simple and compact configuration.

In the microorganism sampling device of one aspect of the present invention, when a sample water drain part for draining sample water remaining in the housing part is provided on the bottom part of the housing, the sample water remaining in the housing can be drained by a simple and compact configuration.

In the microorganism sampling device of one aspect of the present invention, when the rectifying part for swirling the sample water supplied into the tubular filter is provided within the channel of the cap, sample water supplied from the water supply channel of the head part can be supplied as a swirling flow into the tubular filter of the filter part and therefore, it is possible, by a simple and compact configuration, to prevent microorganisms from being adhered to the inner surface of the tubular filter and to peel off microorganisms even when the microorganisms are adhered on the inner surface of the tubular filter.

The microorganism sampling device of one aspect of the present invention includes a base part having a water supply channel and allows a water supply pipe for supplying sample water to be connected to the water supply channel, and therefore, does not need to integrally incorporate the water supply pipe, thus achieving a simple and compact configuration.

In addition, the microorganism sampling device of one aspect of the present invention allows the water supply channel of the head part and the inside of the filter part to communicate with each other by attaching the base part to the lower part of the housing part, thus achieving a simple and compact configuration.

Further, the microorganism sampling device of one aspect of the present invention allows the filter part to be removed from the housing part by removing the housing part from the upper part of the base part and therefore, for example, operations such as cleaning of the housing part and replacement of the tubular filter (for example, as a disposable tubular filter) of the filter part can be easily performed, thus achieving excellent maintainability, too.

In the microorganism sampling device of one aspect of the present invention, when a base part further having a water discharge channel is provided and a water discharge pipe for discharging sample water can be connected to the water discharge channel, it is not necessary to integrally incorporate the water discharge pipe; thus achieving a further simple and compact configuration.

In addition, in the microorganism sampling device of one aspect of the present invention, when the housing part is attached to the upper part of the base part and thereby, the water discharge channel of the base part and a space outside the filter part is made to communicate with each other, it is not necessary to provide an overflow pipe. In accordance with this, a further simple and compact configuration can be achieved.

In addition, in the microorganism sampling device of one aspect of the present invention, the head part, housing part, and filter part are assembled and thereby, the sample water supplied from the water supply channel of the base part can be supplied into the tubular filter of the filter part and the sample water having passed through the tubular filter can be discharged from the water discharge channel of the base part; thus achieving a simple and compact configuration.

Further, the microorganism sampling device of one aspect of the present invention is configured such that the sample water supplied from the water supply channel of the base part can be supplied into the tubular filter of the filter part and the sample water having passed through the tubular filter can be discharged from the water discharge channel of the head part; thus allowing a large amount of sample water to be continuously treated.

In the microorganism sampling device of one aspect of the present invention, when a concentrated water discharge part for discharging the concentrated water from the cup is provided on the base part by inserting a pipe for discharging concentrated water in which microorganisms that are too large to pass through the tubular filter are concentrated, the concentrated water stored in the cup can be collected by a simple and compact configuration.

The microorganism sampling device of one aspect of the present invention does not need to provide a sample water drain part for draining the sample water that remains in the housing part, thus achieving a simple and compact configuration.

When the microorganism sampling device of one aspect of the present invention is a portable device including a frame having a stand on its back surface and fixing the microorganism sampling device according to any one of the above descriptions to the frame, it becomes easy to carry and in combination with the simple and compact configuration, can be brought and used at the site of sampling.

In addition, when the microorganism sampling device of one aspect of the present invention, which is the portable-type device described above, is attached to a backpack-type frame, one worker can easily bring it into a ship. Further, in sampling ballast water, the portable microorganism sampling device is removed from the backpack-type frame and installed by using the stand, thereby enabling its use in a stable state.

Advantageous Effects of Invention

According to the present invention, the microorganism sampling device that has a simple and compact configuration and also has excellent maintainability can be provided.

DESCRIPTION OF EMBODIMENTS

Embodiments of the present invention will be described with reference to the drawings.

Figure 1:
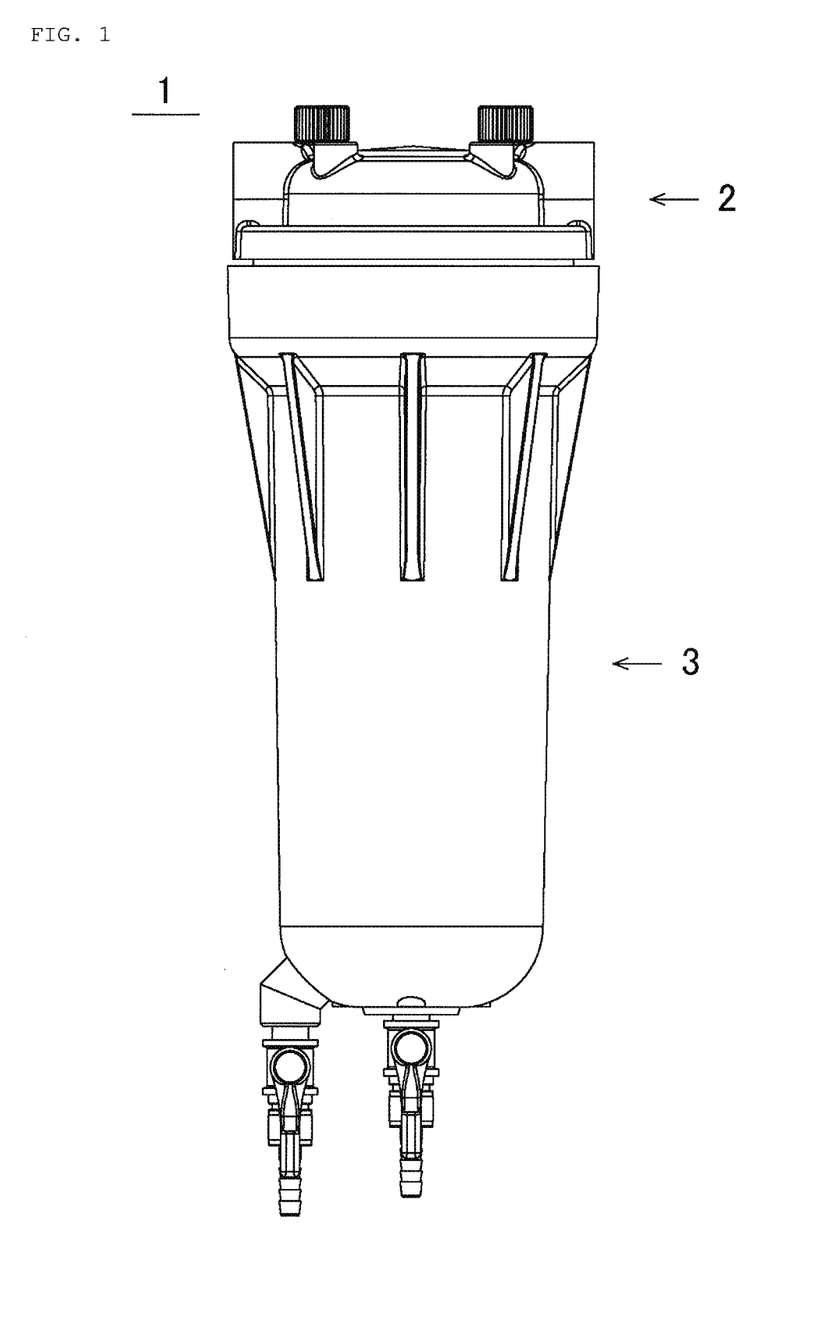
FIG. 1 shows a front view of a microorganism sampling device in an embodiment of the present invention.
Figure 2:
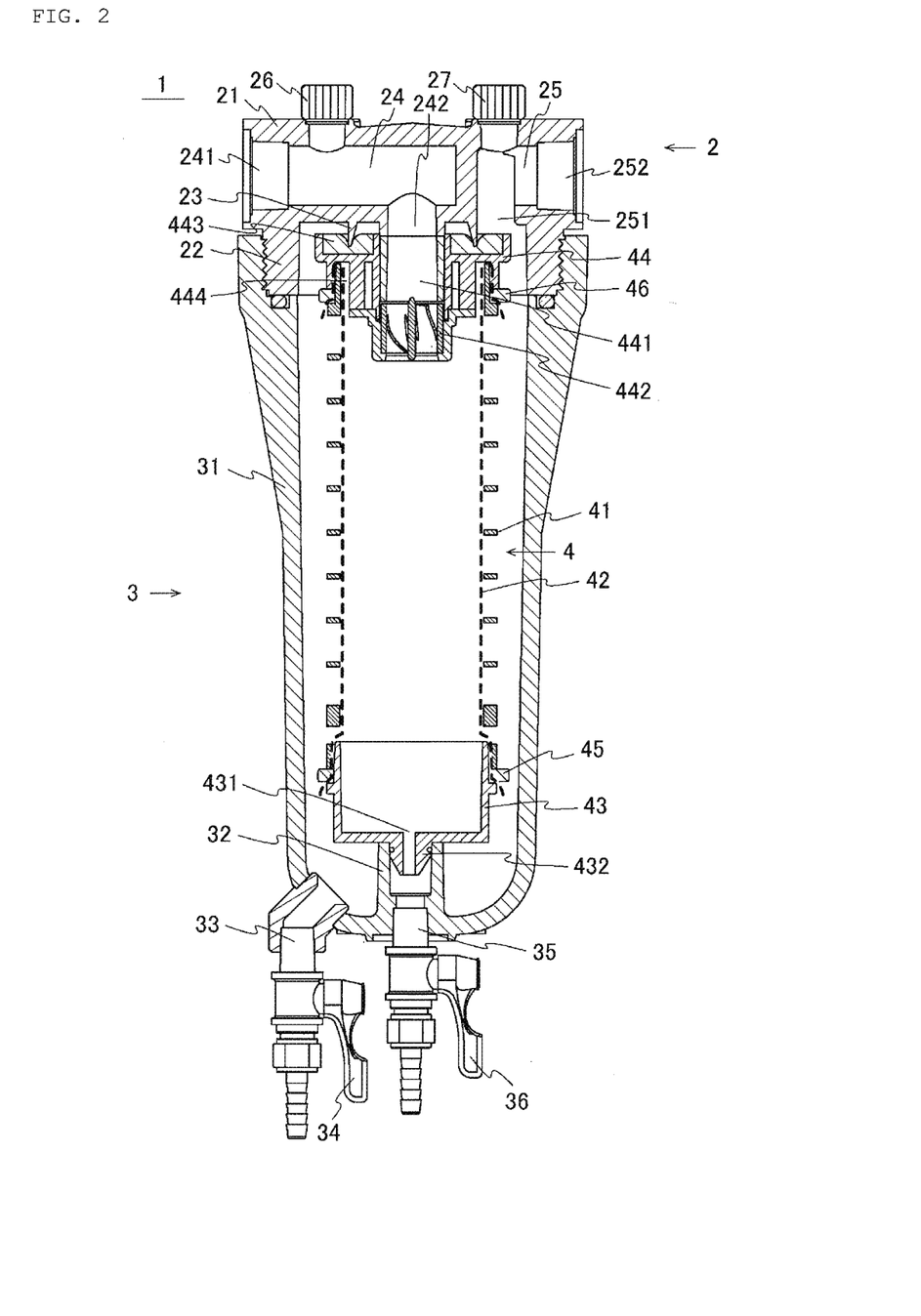
FIG. 2 shows a longitudinal sectional view of the microorganism sampling device shown in FIG. 1.
Figure 3:
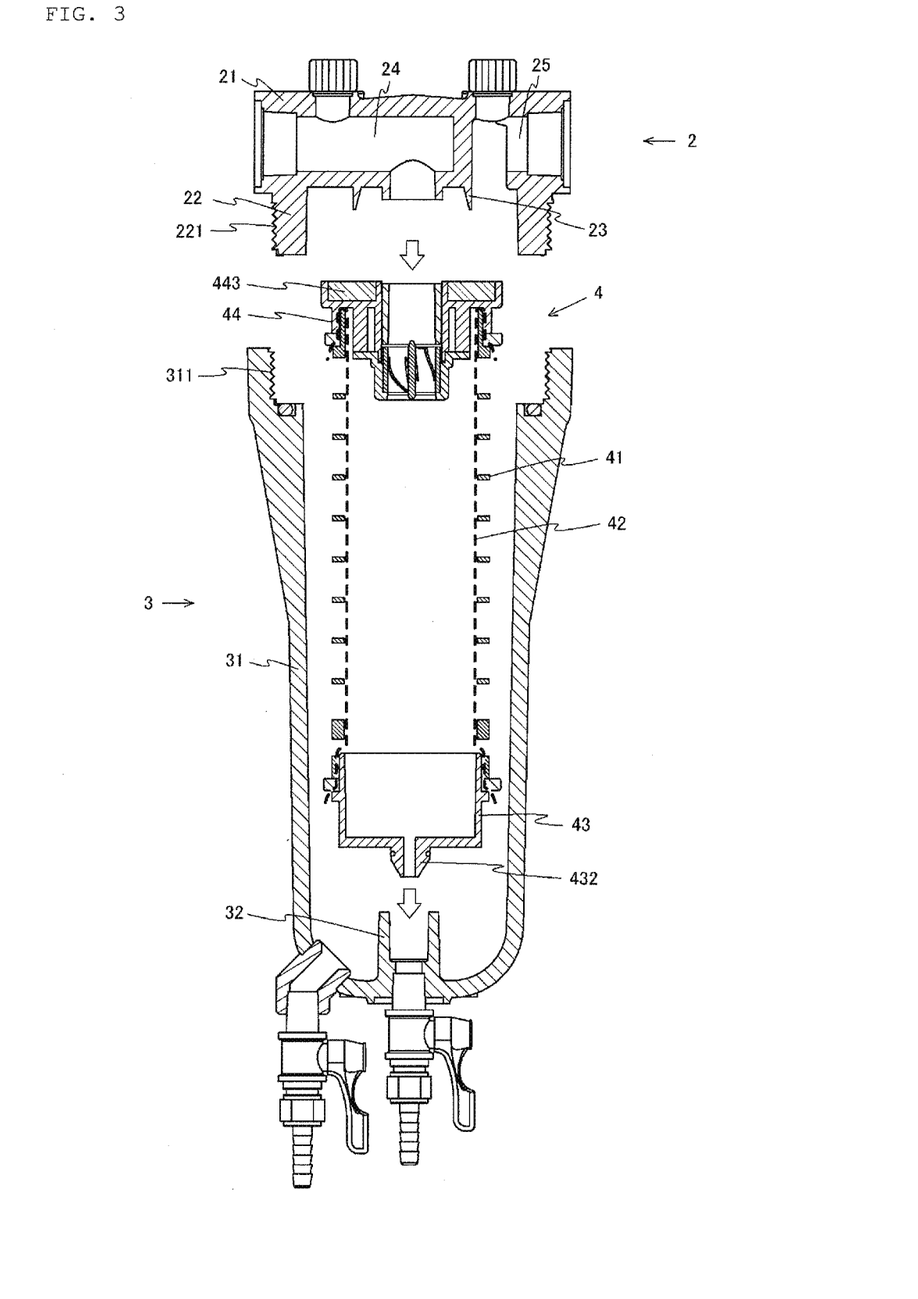
FIG. 3 shows an exploded view of the microorganism sampling device shown in FIG. 1.

FIG. 1 shows a front view of a microorganism sampling device in an embodiment of the present invention. FIG. 2 shows a longitudinal sectional view of the microorganism sampling device shown in FIG. 1. FIG. 3 shows an exploded view of the microorganism sampling device shown in FIG. 2.

A microorganism sampling device 1 in the embodiment of the present invention includes a head part 2, a housing part 3 to the upper part of which the head part 2 is detachably attached, and a filter part 4 which is housed in the housing part 3.

The head part 2 has a head body 21 for supplying and discharging sample water, a cylindrical part 22 formed on a lower surface outer peripheral part of the head body 21, and an annular seal part 23 formed on a lower surface of the head body 21 and on a side closer to the center than the cylindrical part 22.

The head body 21 internally has a water supply channel 24 for supplying sample water and a water discharge channel 25 for discharging the sample water.

The water supply channel 24 has an inflow port 241 formed on a side surface of the head body 21 and has an outflow port 242 formed in the center on a lower surface of the head body 21. To the inflow port 241, a water supply pipe for supplying sample water, the pipe being not illustrated, can be connected.

In addition, the water discharge channel 25 has an inflow port 251 formed between the cylindrical part 22 and the annular seal part 23 on a lower surface of the head body 21 and has an outflow port 252 formed at a position opposite to the inflow port 241 of the water supply channel 24 on a side surface of the head body 21. To the outflow port 252, a water discharge pipe, which is not illustrated, for discharging sample water can be connected.

On an outer peripheral surface of the cylindrical part,22, a male screw part 221 which is engaged with a female screw part 311 formed on an upper inner peripheral surface of a housing body 31 described later is formed.

In addition, on an upper part of the head body 21, air intake parts 26 and 27 for taking in air respectively into the water supply channel 24 and the water discharge channel 25 are formed.

The housing part 3 has the housing body 31 having an opening on its upper part and composed of a tubular container for housing the filter part 4 from the opening on the upper part, and a cylindrical fitting concave part 32 erected in the center of a bottom part of the housing body 31.

On the bottom part of the housing body 31, a drain pipe 33 is provided, and a drain cock 34 is provided on the drain pipe 33.

In the center of the bottom part of the housing body 31, a sample takeout pipe 35 communicating with the fitting concave part 32 is provided. On the sample takeout pipe 35, a sample takeout cock 36 is provided.

On the upper inner peripheral surface of the housing body 31, the female screw part 311 is formed. With the female screw part 311, the male screw part 221 formed on the outer peripheral surface of the cylindrical part 22 of the head part 2 is engaged, and the head part 2 is detachably attached to the upper part of the housing part 3.

The filter part 4 has a reinforcing tube 41 that has a frame structure and a mesh shape, a tubular mesh filter 42 made of resin that is arranged within the reinforcing tube 41, a cup 43 that communicates with a lower opening of the tubular mesh filter 42, and a cap 44 that has a channel 441 communicating with an upper opening of the tubular mesh filter 42.

A discharge port 431 is provided in the center of a bottom part of the cup 43 and a cylindrical insertion convex part 432 communicating with the discharge port 431 is suspendedly provided on a lower surface of the bottom part of the cup 43.

In the flow channel 441 of the cap 44, a rectifying member 442 for swirling the sample water supplied into the tubular mesh filter 42 is arranged. In addition, an annular packing 443 is installed on an upper surface of the cap 44.

The cup 43 is attached to a lower end of the reinforcing tube 41 by inserting an upper part of the cup 43 to the lower opening of the tubular mesh filter 42 whose lower end is exposed toward a lower part of the reinforcing tube 41 and further by fitting the upper part of the cup 43 to a lower inner surface of the reinforcing tube 41 via the engagement O-ring 45.

The cap 44 is attached to an upper end of the reinforcing tube 41 by folding an upper part of the tubular mesh filter 42 at the upper end of the reinforcing tube 41 and engaging it on an outer peripheral surface of the reinforcing tube 41 by an engagement O-ring 46, and then, fitting an annular concave part 444 formed on a lower surface of the cap 44 to the upper end of the reinforcing tube 41.

As shown in FIG. 3, the microorganism sampling device 1 in the embodiment of the present invention can be assembled by housing the filter part 4 in the housing part 3 and after that, screwing the head part 2 to the upper part of the housing 3.

In housing the filter part 4 in the housing part 3, the insertion convex part 432 of the cup 43 is inserted to the fitting concave part 32 of the housing body 31 in a fit state, thereby having a bottom part of the filter part 4 supported by a bottom part of the housing part 3.

In addition, in screwing the head part 2 to the upper part of the housing part 3, the male screw part 221 formed on the outer peripheral surface of the cylindrical part 22 of the head part 2 is engaged with the female screw part 311 formed on the upper inner peripheral surface of the housing body 31, thereby having the head part 2 detachably attached to the upper part of the housing part 3.

In this case, due to engagement of both the screw parts of the head part 2 and the housing part 3, the annular seal part 23 of the head part 2 bites into the annular packing 443 which is installed on the upper surface of the cap 44 of the filter part 4 and a lower end part of the outflow port 242 of the water supply channel 24 of the head part 2 abuts on an upper end part of the channel 441 of the cap 44, thereby having the water supply channel 24 of the head part 2 and the channel 441 of the cap 44 communicate with each other. In addition, the water discharge channel 25 of the head part 2 and a space that is outside the filter part 4 within the housing part 3 communicate with each other.

The filter part 4 housed in the housing part 3 is held so as not to move between the head part 2 and the housing part 3.

As shown in FIG. 2, in the microorganism sampling device 1 in the embodiment of the present invention, sample water supplied from a water supply pipe, which is not illustrated, is supplied from the water supply channel 24 formed on the head body 21 of the head part 2 into the tubular mesh filter 42 via the channel 441 formed in the cap 44 of the filter part 4.

In addition, the sample water having passed through the tubular mesh filter 42 reaches a space outside the filter part 4 within the housing part 3 and is discharged from the water discharge channel 25 formed on the head body 21 of the head part 2. In this case, the microorganisms having a size L that is too large to allow passing through the tubular mesh filter 42 remain within the tubular mesh filter.

Here, in the flow channel 441 of the cap 44, the rectifying member 442 for swirling the sample water supplied into the tubular mesh filter 42 is provided. Accordingly, the sample water supplied from the water supply channel 24 of the head body 21 can be supplied as a swirling flow into the tubular mesh filter 42 and therefore, microorganisms are prevented from being adhered to the inner surface of the tubular mesh filter 42 and can be peeled off even when the microorganisms are adhered on the inner surface of the tubular mesh filter 42.

After a predetermined amount of sample water has been supplied, the drain cock 34 provided in the housing part 3 is opened and thereby the sample water remaining within the housing body 31 can be drained from the drain pipe 33.

In addition, after the sample water remaining within the housing body 31 has been drained, the sample takeout pipe 35 provided in the housing part 3 is opened and thereby, concentrated water in which microorganisms stored in the cup 43, which are too large to pass through the tubular mesh filter 42, are concentrated can be collected from the sample takeout pipe 35.

In the microorganism sampling device 1 in an embodiment of the present invention, the head body 21 of the head part 2 internally has the water supply channel 24 for supplying sample water and the water discharge channel 25 for discharging the sample water, and the water supply pipe for supplying the sample water can be connected to the water supply channel 24 and the water discharge pipe for discharging the sample water can be connected to the water discharge channel 25; and therefore, it is not necessary to integrally incorporate a water supply pipe and a water discharge pipe as in the sampling device described in Patent Literature 1, thus achieving a simple and compact configuration.

Further, in the microorganism sampling device 1 in the embodiment of the present invention, the sample water supplied from the water supply channel 24 of the head part 2 can be supplied into the tubular mesh filter 42 of the filter part 4 and the sample water having passed through the tubular mesh filter 42 can be discharged from the water discharge channel 25 of the head part 2; and therefore, it is not necessary to provide an overflow pipe as in the sampling device described in Patent Literature 1, thus achieving a simple and compact configuration.

In the microorganism sampling device 1 in an embodiment of the present invention, the filter part 4 can be removed from inside of the housing part 3 by removing the head part 2 from the upper part of the housing part 3 and therefore, for example, operations such as cleaning of the housing part 3 and replacement of the tubular mesh filter 42 (for example, as a disposable tubular filter) can be easily performed, thus achieving excellent maintainability.

Further, the microorganism sampling device 1 in the embodiment of the present invention is configured such that sample water supplied from the water supply channel 24 of the head part 2 can be supplied into the tubular mesh filter 42 of the filter part 4 and the sample water having passed through the tubular filter can be discharged from the water discharge channel of the head part 2, thus allowing a large amount of sample water to be continuously treated.

Figure 4:
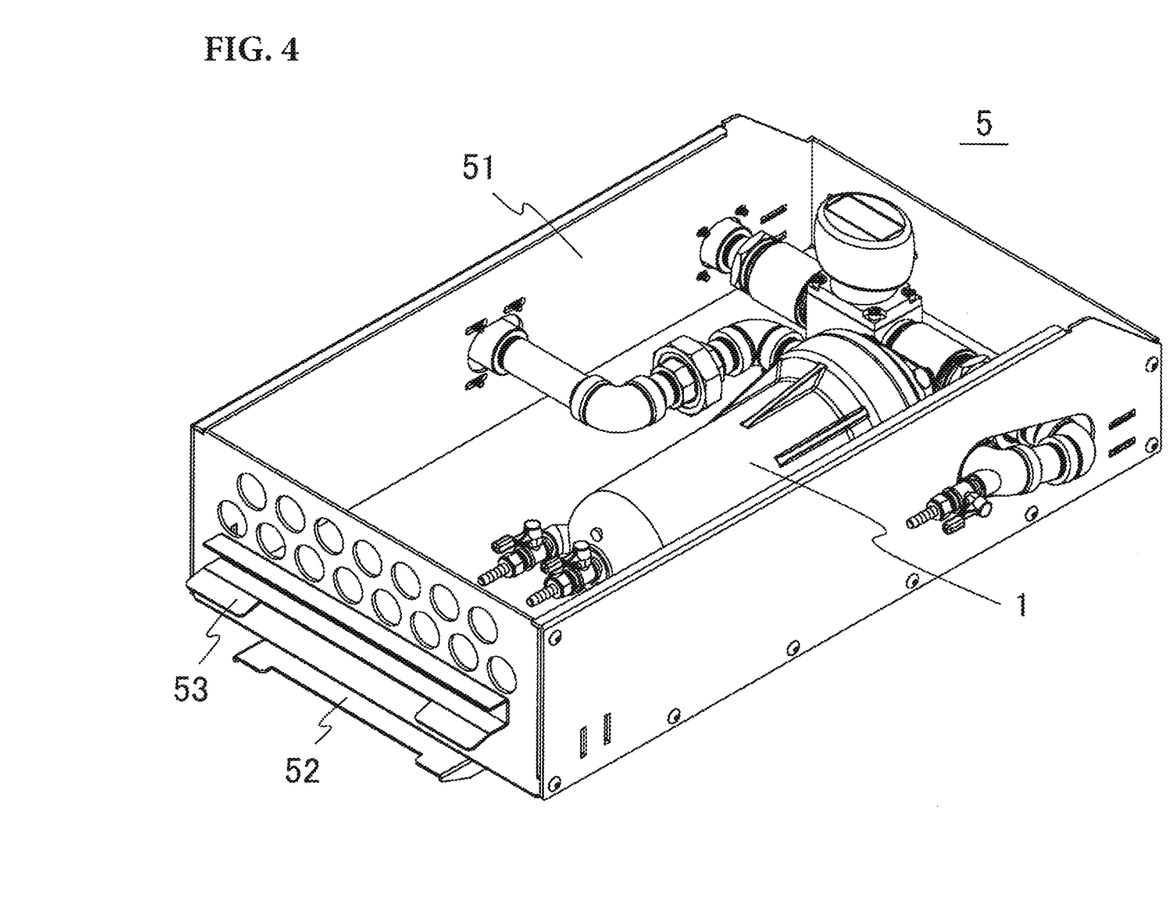
FIG. 4 shows a perspective view in a case where the microorganism sampling device shown in FIG. 1 is a portable device.
Figure 5:
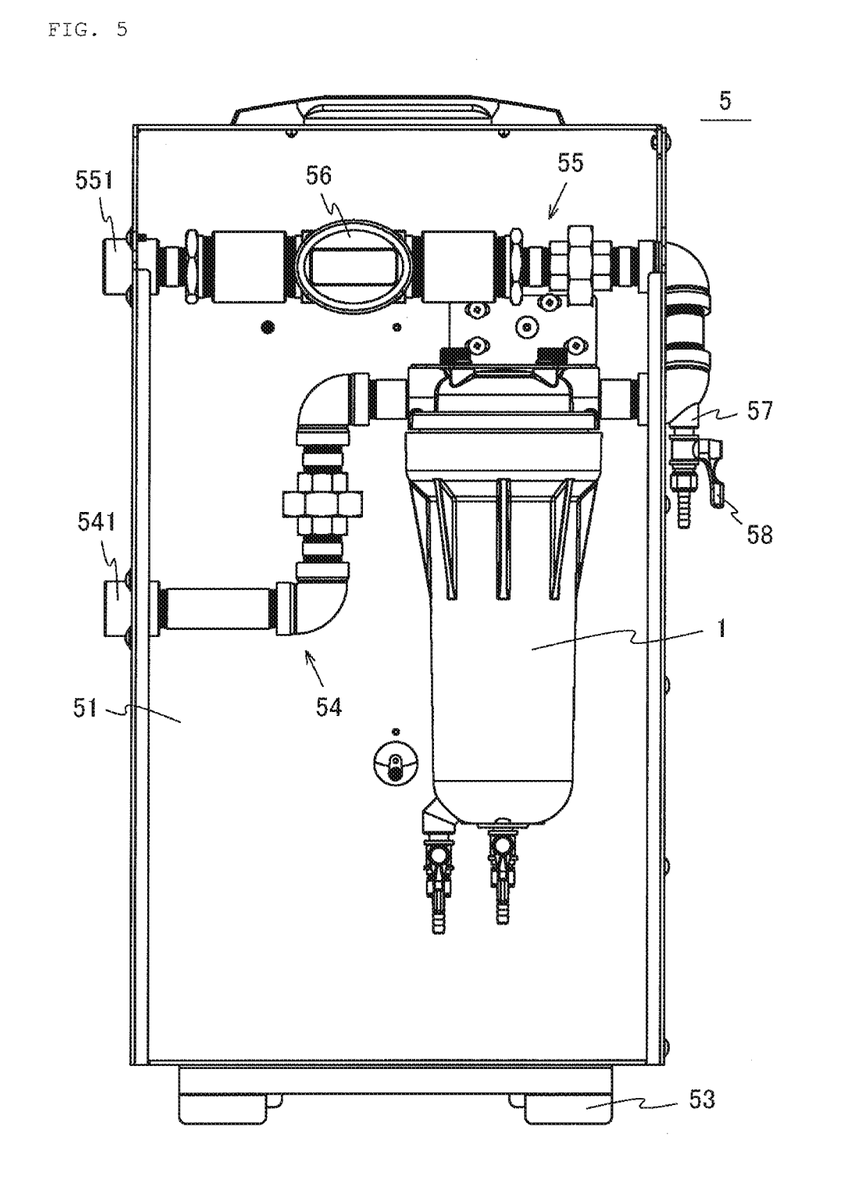
FIG. 5 shows a front view of the device shown in FIG. 4.
Figure 6:
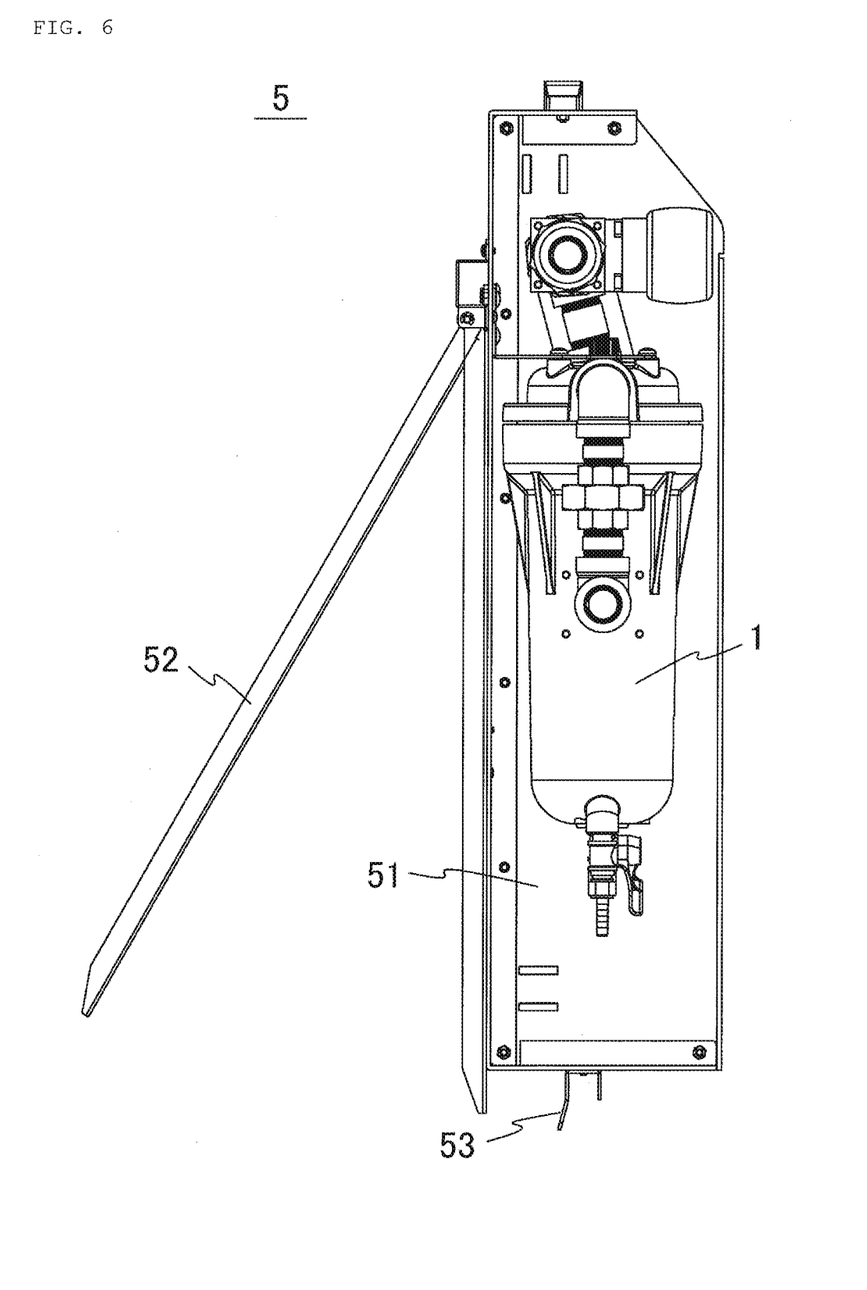
FIG. 6 shows a left side view of the device shown in FIG. 5.

FIG. 4 shows a perspective view of the microorganism sampling device 1 shown in FIG. 1 when the device is of a portable type. FIG. 5 shows a front view of the device shown in FIG. 4. FIG. 6 shows a left side view of the device shown in FIG. 5 in the state where the left side plate of the frame has been removed.

The microorganism sampling device 1 in an embodiment of the present invention can be provided as a portable microorganism sampling device 5 by being fixed to a frame 51 having a stand 52 on its back surface and foot fittings 53 on its bottom surface. In the examples shown in FIG. 4 to FIG. 6, the frame 51 is a box-shaped one whose one surface is opened.

As shown in FIG. 4 to FIG. 6, when the microorganism sampling device 1 in the embodiment of the present invention is provided as the portable device 5, for example, a water supply pipe 54 for supplying sample water to the microorganism sampling device 1 and a water discharge pipe 55 for discharging the sample water from the microorganism sampling device 1 can be integrally installed to the frame 51. In addition, on the water discharge pipe 55, a flowmeter 56 for measuring the amount of sample water can be installed.

When joints 541 and 551 connectable to various types of pipes are provided at each end of the water supply pipe 54 and the water discharge pipe 55, connection to any sample water supply pipe is possible regardless of its type.

In the middle of the water discharge pipe 55, a second sample takeout pipe 57 can be provided. In addition, in the second sample takeout pipe 57, a second sample takeout cock 58 can be provided.

By opening the second sample takeout cock 58 while sample water is supplied to the portable microorganism sampling device 5, sample water containing microorganisms having a size S that allows passing through the tubular mesh filter 42 of the filter part 4 can be extracted from the second sample takeout pipe 57.

In the embodiment of the present invention, when the microorganism sampling device 1 is provided as the portable device 5, it becomes easy to carry and in combination with the simple and compact configuration, and can be brought and used at the site of sampling.

In addition, in the embodiment of the present invention, when the portable microorganism sampling device 5 is attached to a backpack-type frame, which is not illustrated, it can be easily brought into a ship by one worker. Further, in sampling ballast water, the portable microorganism sampling device 5 is removed from the backpack-type frame and installed by using the stand 52 and the foot fittings 53, thereby enabling its use in a stable state.

In the above embodiment of the present invention, the tubular mesh filter 42 made of resin is used in the filter part 4; however, other types of tubular filters can be used.

Figure 7:
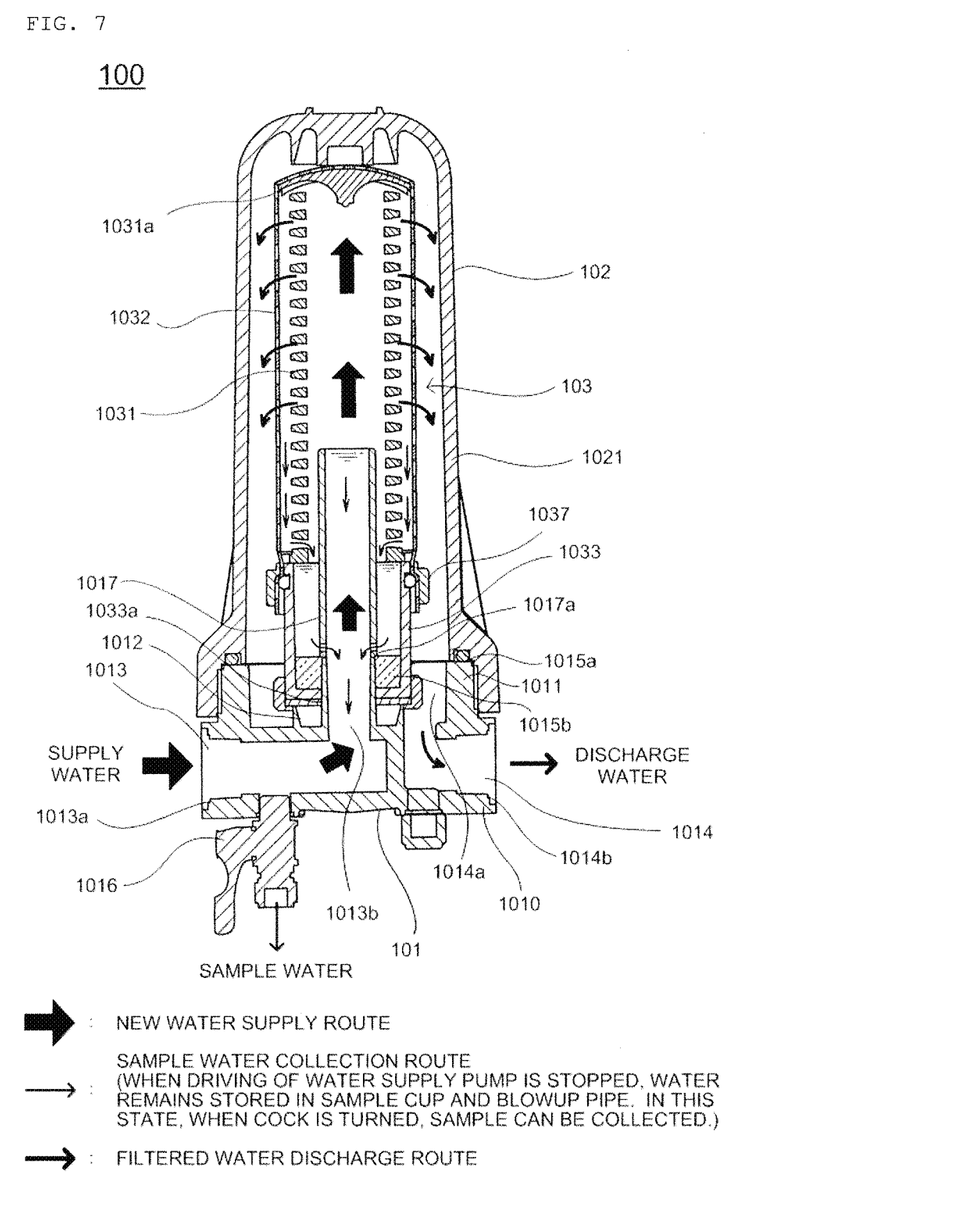
FIG. 7 shows a longitudinal sectional view of a microorganism sampling device in another embodiment of the present invention.

A microorganism sampling device in another embodiment of the present invention will be described. FIG. 7 shows a longitudinal sectional view of the microorganism sampling device in the other embodiment of the present invention. A microorganism sampling device 100 includes a base part 101, a housing part 102 which is detachably attached to an upper part of the base part 101, and a filter part 103 which is housed in the housing part 102.

The base part 101 has a base body 1010 for supplying and discharging sample water, a cylindrical part 1011 formed on an upper surface outer peripheral part of the base body 1010, and an annular seal part 1012 formed on the side closer to the center than the cylindrical part 1011 on an upper surface of the base body 1010.

The filter part 103 has a rectifying tube 1031 that has a frame structure and adjusts a water flow, a filtering mesh filter 1032 that is arranged outside the rectifying tube 1031, and a sample cup 1033 that communicates with a lower opening of the filtering mesh filter 1032. The rectifying tube 1031 has a cap 1031*a* on its upper part. In the center of a bottom part of the sample cup 1033, an opening 1033*a* through which a pipe 1017 described later can penetrate is provided. In addition, the sample cup 1033 has an effect of enabling a dynamic water flow to be statically suppressed and therefore, damages to microorganisms caused by the water flow can be reduced as much as possible. It should be noted that although a pipe 1071 is not necessarily used, the pipe 1071 is preferable to be used so as to reduce damages to microorganisms caused by the water flow as much as possible.

The base body 1010 internally has a water supply channel 1013 for supplying sample water and a water discharge channel 1014 for discharging the sample water. In the water supply channel 1013, an inflow port 1013a is provided on a side surface of the base body 1010 and an outflow port 1013b is provided in the center of the upper surface of the base body 1010. To the inflow port 1013a, a water supply pipe, which is not illustrated, for supplying sample water can be connected.

In the center of the upper surface of the base body 1010, the pipe 1017 is provided at the outflow port 1013b. It is preferable that the pipe 1017 has such a height that when the filter part 103 is attached to the base part 101, its tip part does not reach the cap 1031a. On a side surface at a predetermined position of the pipe 1017, one or more through holes 1017a are provided. The through holes 1017a are provided so that concentrated sample water stored in a sample cup 1013 is passed through the pipe 1017 and is collected outside the microorganism sampling device 100. In addition, on a lower part of the base body 1010, a sample water takeout cock 1016 for draining sample water is provided.

In the water discharge channel 1014, an inflow port 1014a is formed between the cylindrical part 1011 and the annular seal part 1012 on the upper surface of the base body 1010 and an outflow port 1014b is formed at a position on the opposite side to the inflow port 1013a of the water supply channel 1013 on the side surface of the base body 1010. To the outflow port 1014b, a pipe, which is not illustrated, for discharging sample water can be connected.

The housing part 102 has a housing body 1021 that is composed of a tubular container having an opening at its lower part and housing the filter part 103 from the opening. In attaching the housing part 102 to the base part 101, a rubber packing 1015a is used for watertightness.

On an outer peripheral surface of the cylindrical part 1011, a male screw part (not illustrated) which is engaged with a female screw part (not illustrated) formed on a lower inner peripheral surface of the housing body 1021 of the housing part 102 is formed.

Before the attachment of the housing part 102 to the base part 101, the filter part 103 is installed on the base 101. The pipe 1017 is penetrated from the tip side of the pipe 1017 to the opening 1033a provided on the sample cup 1033, and the sample cup 1033 is positioned to be fixed to the annular seal part 1012.

The filtering mesh filter 1032, which is arranged outside the rectifying tube 1031, covers the cap 1031a and a side surface of the rectifying tube 1031; and its lower part covers an upper outer periphery of the sample cup 1033. Further, by using an engagement annular member 1037 from above the filtering mesh filter 1032, the lower end part of the filtering mesh filter 1032 and the upper part of the sample cup 1033 are fastened for fixing.

On the bottom surface of the sample cup 1033, a rubber packing 1015b is arranged. The rubber packing 1015b prevents concentrated sample water from leaking from a gap between an outer peripheral surface of the pipe 1017 and an inner peripheral surface of the opening 1033a of the sample cup 1033. The through holes 1017a provided on the pipe 1017 are provided in the position of an upper surface of the packing 1015b, thereby allowing the sample water stored in the sampling cup 1003 all to be drained.

As shown in FIG. 7, in the microorganism sampling device 100, sample water supplied from a water supply pipe, which is not illustrated, flows in from the water supply channel 1013 formed on the base body of the base part 101, and spouts to the inside of the filter part 103 from the pipe 1017 from which the sample water blows up to the inside of the filter part 3 in a fountain-like manner.

The sample water that has blown up from the pipe 1017 is rectified by being passed through gaps on the frame-structured rectifying tube 1031 and the cap 1031a; and the sample water is supplied to the filtering mesh filter 1032 from the inside. In addition, the sample water having passed through the filtering mesh filter 1032 reaches a space outside the filter part 103 within the housing part 102 and is discharged from the water discharge channel 1014 formed on the base part 101. After a predetermined amount of sample water has been supplied, the sample water after filtering is not retained in the housing and is discharged outside the housing part 3 via the water discharge channel 1014.

The microorganisms having a size L that is too large to allow passing through the filtering mesh filter 1032 remain within the filtering mesh filter 1032.

Concentrated sample water remains within the sample cup 1033. When the supply of sample water is stopped, water remains stored within the sample cup 1033 and pipe 1017. In this state, when the sample water takeout cock 1016 is opened, the concentrated sample water can be collected.

In this embodiment, it is not necessary to provide pipes and sample water supply and discharge openings in the housing part, thus the configuration is easy. In addition, after the supply of a predetermined amount of sample water, the concentrated sample water can be collected only by opening the sample water takeout cock 1016 and thus, the operation is simplified. The filtered sample water is not retained in the housing part 102.

In addition, the above embodiment of the present invention takes as an example the case in which microorganisms such as planktons existing in ballast water are sampled; however, it is also applicable to the case in which microorganisms existing in other types of water, for example, such as river water and sewage, are sampled.

It should be noted that the head part 2 and the base part 101 are collectively referred to as the lid part in the present description.

The present invention is not limited to the embodiments described above and the configuration may be changed as appropriate without departing from the scope of the invention as a matter of course.

INDUSTRIAL APPLICABILITY

The microorganism sampling device of the present invention has a simple and compact configuration and also has excellent maintainability, thus providing a high practical value.

REFERENCE SIGNS LIST

1 microorganism sampling device
2 head part
21 head body
22 cylindrical part
221 male screw part
23 annular seal part
24 water supply channel
241 inflow port 242 outflow port
25 water discharge channel
251 inflow port
252 outflow port
26 air intake part
27 air intake part
3 housing part
31 housing body
31 female screw part
32 fitting concave part
33 drain pipe
34 drain cock
35 sample takeout pipe
36 sample takeout cock
4 filter part
41 reinforcing tube
42 tubular mesh filter
43 cup
431 discharge port
432 insertion convex part
44 cap
441 channel
442 rectifying member
443 annular packing
444 annular concave part
45 engagement O-ring
46 engagement O-ring
5 portable microorganism sampling device
51 frame
52 stand
53 foot fitting
54 water supply pipe
541 joint
55 water discharge pipe
551 joint
56 flowmeter
57 second sample takeout pipe
58 second sample takeout cock
100 microorganism sampling device
101 base part
1010 base body
1011 cylindrical part
1012 annular seal part
1013 water supply channel
1013a inflow port
1013b outflow port
1014 water discharge channel
1014a inflow port
1014b outflow port
1015a rubber packing
1015b rubber packing
1016 sample water takeout cock
1017 pipe
1017a through hole
102 housing part
1021 housing body
103 filter part
1031 rectifying tube
1013a cap
1032 filtering mesh filter
1033 sample cup
1033a opening
1037 engagement annular member

The invention claimed is:

1. A microorganism sampling device for sampling microorganisms existing in water, comprising:
a lid part having a water supply channel allowing a water supply pipe to be connected thereto, the water supply pipe being for supplying sample water;
a housing part, the lid part being detachably attached to the housing part or the housing part being detachably attached to the lid part; and
a filter part housed in the housing part and filtering the microorganisms from the sample water, wherein
the lid part is a base part;
the housing part is detachably attached to an upper part of the base part;
the base part includes an opening for supplying to an inside of the filter part the sample water supplied to the base part;
the filter part has a tubular filter and a cup, the cup being attached so as to communicate with the tubular filter;
the cup has an opening at a bottom part of the cup and the bottom part of the cup is supported by the base part; and
the sample water is supplied from an opening provided on the base part to the inside of the filter part via the opening provided on the bottom part of the cup.

2. A portable microorganism sampling device comprising a frame with a stand provided on a back surface; wherein the microorganism sampling device according to claim 1 is fixed to the frame.

3. A microorganism sampling device for sampling microorganisms existing in water, comprising:
a lid part having a water supply channel allowing a water supply pipe to be connected thereto, the water supply pipe being for supplying sample water;
a housing part, the lid part being detachably attached to the housing part or the housing part being detachably attached to the lid part; and
a filter part housed in the housing part and filtering the microorganisms from the sample water, wherein
the lid part is a base part;
the housing part is detachably attached to an upper part of the base part,
the base part includes a pipe for supplying to an inside of the filter part the sample water supplied to the base part,
the filter part has a tubular filter and a cup, the cup being attached so as to communicate with the tubular filter; and
the cup has a through hole for inserting the pipe on a bottom part of the cup and the bottom part of the cup is supported by the base part.

4. The microorganism sampling device according to claim 3, wherein
the base part further has a water discharge channel allowing a water discharge pipe to be connected thereto, the water discharge pipe being for discharging the sample water having passed through the filter part; and
the base part is attached to a lower part of the housing part so as to make the water discharge channel of the base part and a space outside the filter communicate with each other, thereby allowing the sample water having passed through the tubular filter of the filter part to be discharged from the water discharge channel of the base part.

5. The microorganism sampling device according to claim 4, wherein
the pipe includes an outflow port so as to discharge concentrated water from the cup, the concentrated water being such that microorganisms too large to pass through the tubular filter are concentrated; and the base part includes a concentrated water discharge part for discharging the concentrated water flowing out from the outflow port of the pipe.

6. The microorganism sampling device according to claim 4, wherein the filter part includes a frame-structured tubular body provided on an inside of the tubular filter and supporting the tubular filter.

7. The microorganism sampling device according to claim 3, wherein the pipe includes an outflow port so as to discharge concentrated water from the cup, the concentrated water being such that microorganisms too large to pass through the tubular filter are concentrated; and the base part includes a concentrated water discharge part for discharging the concentrated water flowing out from the outflow port of the pipe.

8. The microorganism sampling device according to claim 3, wherein the filter part includes a frame-structured tubular body provided on an inside of the tubular filter and supporting the tubular filter.

9. A portable microorganism sampling device comprising a frame with a stand provided on a back surface; wherein the microorganism sampling device according to claim 3 is fixed to the frame.

* * * * *